(12) United States Patent
Sceats (10) Patent No.: US 9,913,475 B2
(45) Date of Patent: Mar. 13, 2018

(54) OXIDE PRODUCTS FORMED FROM CALCINED CARBONATE POWDER FOR USE AS BIOCIDE, CHEMICAL DETOXIFIER AND CATALYST SUPPORT PRODUCTS

(71) Applicant: Calix Ltd, Pymble, NSW (AU)

(72) Inventor: Mark Sceats, Pymble (AU)

(73) Assignee: Calix Ltd, Pymble, NSW (AU)

( * ) Notice: Subject to any disclaimer, the term of this patent is extended or adjusted under 35 U.S.C. 154(b) by 0 days.

(21) Appl. No.: 15/106,759

(22) PCT Filed: Dec. 10, 2014

(86) PCT No.: PCT/AU2014/001115
§ 371 (c)(1),
(2) Date: Jun. 20, 2016

(87) PCT Pub. No.: WO2015/100468
PCT Pub. Date: Jul. 9, 2015

(65) Prior Publication Data
US 2017/0035053 A1    Feb. 9, 2017

(30) Foreign Application Priority Data
Jan. 2, 2014  (AU) ................................ 2014900006

(51) Int. Cl.
| | |
|---|---|
| A01N 59/06 | (2006.01) |
| A01N 25/12 | (2006.01) |
| B01J 21/10 | (2006.01) |
| B01J 35/02 | (2006.01) |
| B01J 35/10 | (2006.01) |
| C01F 5/06 | (2006.01) |
| C04B 2/10 | (2006.01) |
| B82Y 40/00 | (2011.01) |

(52) U.S. Cl.
CPC .......... *A01N 59/06* (2013.01); *A01N 25/12* (2013.01); *B01J 21/10* (2013.01); *B01J 35/026* (2013.01); *B01J 35/1019* (2013.01); *C01F 5/06* (2013.01); *C04B 2/102* (2013.01); *C04B 2/106* (2013.01); *B82Y 40/00* (2013.01); *C01P 2004/61* (2013.01); *C01P 2006/12* (2013.01)

(58) Field of Classification Search
CPC ........ A01N 25/12; A01N 59/06; A01N 25/04; B01J 21/10; B01J 35/026; B01J 35/1019; B82Y 40/00; C01F 5/06; C01P 2004/61; C01P 2006/12; C04B 2/102; C04B 2/106
USPC ....................................................... 424/405
See application file for complete search history.

(56) References Cited

U.S. PATENT DOCUMENTS

| | | |
|---|---|---|
| 2,576,731 A | 11/1951 | Thomsen |
| 5,906,804 A | 5/1999 | Aral et al. |
| 6,827,766 B2 | 12/2004 | Carnes et al. |
| 2006/0034743 A1 | 2/2006 | Radway et al. |
| 2008/0102092 A1 | 5/2008 | Sasaya |
| 2009/0041818 A1 | 2/2009 | Otsuki et al. |
| 2011/0223088 A1 | 9/2011 | Chang et al. |
| 2012/0090517 A1 | 4/2012 | Radway |
| 2016/0264435 A1 | 9/2016 | Sceats et al. |

FOREIGN PATENT DOCUMENTS

| | | | |
|---|---|---|---|
| WO | 2007045048 | 4/2007 | |
| WO | 2007045050 A1 | 4/2007 | |
| WO | 2007112496 A1 | 10/2007 | |
| WO | 2008064417 A1 | 6/2008 | |
| WO | 2012145802 A2 | 11/2012 | |
| WO | WO 2012145802 A2 * | 11/2012 | ............. B01J 6/004 |
| WO | 2015100468 A1 | 7/2015 | |

OTHER PUBLICATIONS

International Search Report for International Application No. PCT/AU2014/001115 dated Feb. 16, 2015, 8 pages.
International Written Opinion for International Application No. PCT/AU2014/001115 dated Feb. 16, 2015, 7 pages.
Talari et al., Synthesis, Characterization and Antimicrobial Investigation of Mechanochenucally Processed Silver Doped ZnO Nanoparticles, Chem. Pharm. Bull., (2012) vol. 60, No. 7, pp. 818-824.
Hirano et al., Bacteria in the Leaf Ecosystem with Emphasis on Pseudomonas syringae—a Pathogen, Ice Nucleus, and Epiphyte, Microbiol. Mol. Biol. Rev. (2000), vol. 64, No. 3, pp. 624-653.
Huang et al., Suppression of plant-generated reactive oxygen species is required for successful infection by the rice blast fungus, Virulence, 2:6, 1-4; Nov./Dec. 2011, pp. 559-562.
Vol'nov et al., Thermal Stability of Magnesium Peroxide, N.S. Kurnakov Institute of General and Inorganic Chemistry, Academy of Sciences of the USSR,Jan. 1970, No. 1, pp. 13-18.
Sawai et al., Antibacterial Characteristics of Magnesium Oxide Powder, World Journal of Microbiology and Biotechnology, vol. 16, Issue 2, (2000), pp. 187-194.

(Continued)

*Primary Examiner* — Johann R Richter
*Assistant Examiner* — Courtney Brown
(74) *Attorney, Agent, or Firm* — TraskBritt (57) ABSTRACT

A process and apparatus for manufacture of oxide products for use as biocide, chemical detoxifying, and catalytic support products, from caustic calcined carbonate powder, preferably from magnesite, dolomite, or hydromagnesite, is described. These oxide particles are characterized by high surface area, high porosity and a high degree of calcination, and the method of manufacture utilizes an indirectly heated counterflow reactor. The oxides may be used as a powder, granules, or formulated into a slurry and used as a spray, emulsion, foam or fog, or the powder product may be directly applied. Also described is the formation of particles with microstructures defined by at least one nano-crystalline structure positioned on the outer surface of the particles.

20 Claims, 1 Drawing Sheet

(56) References Cited

OTHER PUBLICATIONS

Yin et al., Antibacterial Activities of Magnesium Oxide Nanoparticles Against Foodborne Pathogens, J. Nanopart. Res., (2011), vol. 13, pp. 6877-6885.
Extended European Search Report for European Application No. 14877351.8, dated May 11, 2017, six pages.
Motoike et al. "Antiviral activities of heated dolomite powder," Biocontrol Sci. 13(4):131-8 (2008).

* cited by examiner

OXIDE PRODUCTS FORMED FROM CALCINED CARBONATE POWDER FOR USE AS BIOCIDE, CHEMICAL DETOXIFIER AND CATALYST SUPPORT PRODUCTS

CROSS-REFERENCE TO RELATED APPLICATIONS

This application is a national phase entry under 35 U.S.C. § 371 of International Patent Application PCT/AU2014/001115, filed Dec. 10, 2014, designating the United States of America and published in English as International Patent Publication WO 2015/100468 A1 on Jul. 9, 2015, which claims the benefit under Article 8 of the Patent Cooperation Treaty to Australian Patent Application Serial No. 2014900006, filed Jan. 2, 2014.

TECHNICAL FIELD

The present disclosure relates broadly to a process and apparatus for manufacture of bio-active materials from calcined powders produced from the flash calcination of materials, where the bioactivity applies to a broad spectrum of viruses, bacteria, fungi and as either a biocide or probiotic depending on the target.

BACKGROUND

There has been an extensive development of nano-materials with biocide and probiotic properties and, in particular, of nano-magnesia MgO and nano-zinc oxide ZnO. An example of a biocide is "Antibacterial characteristics of magnesium oxide powder," J. Sawei et al., *World Journal of Microbiology and Biotechnology* 16, Issue 2, pp. 187-194 (2000), and T. Yin and Y. He, "Antibacterial activities of magnesium oxide nanoparticles against foodborne pathogens," *J. Nanopart. Res.* 13:6877-6885.

In the study by Sawai et al., the objective was to make high surface area MgO with particle sizes below about 50 nm. In trials of these materials, the MgO particles rapidly react with water to form nano-magnesium hydroxide $Mg(OH)_2$. Prior art references to nano-MgO are ascribed herein to nano-$Mg(OH)_2$. These hydrated nano-materials exhibit broad-spectrum bioactivity response to virus, bacteria and fungi. The powder, and the hydrated nano-powder, has as an ability to deactivate toxic materials such as chemical warfare agents.

In a paper published by T. Yin and Y. Lu, it was demonstrated that nano-MgO particles had a strong biocide activity against two foodborne pathogens, namely *Escherichia Coli* and *Salmonella*. This work is important because nano-MgO/$Mg(OH)_2$ is not believed to be toxic to humans or animals, and has a positive impact on plants through the supply of magnesium as a fertilizer. For example, seven log reductions in *E. Coli* were observed at a dosage rate of 8 g/liter solids, and dosages of 1 g/liter suppressed growth, and that 3 g/liter would kill all cells within 24 hours. While $Mg(OH)_2$ is relatively insoluble, it rapidly dissolves in low pH environments, especially at the pH of digestive systems. This would be true of nano-MgO/$Mg(OH)_2$ because the dissolution rate is faster the higher the surface area.

U.S. Pat. No. 6,827,766 B2 claims a decontamination product comprising nano-particles including MgO and $Mg(OH)_2$, selective biocides and a liquid carrier, including water. The biocide properties are significantly enhanced by the presence of the nano-particles. The decontamination processes include a liquid spray, fog, aerosol paste, gel, wipe, vapor or foam. While the claims are limited to the requirement of adding an existing biocide as an adjuvant to the product, the examples disclosed teach that the nano-particles, in the liquid carriers, had an effective, long-term biocide activity without the adjuvant. Specifically, their example 3 shows that a ratio of 5/1 water/oil emulsion with 2% nano-MgO, CaO, and ZnO solids had such properties, notably without the requirement of a biocide.

The impact of the particle size would seem to be important. U.S. Pat. No. 2,576,731 (Thomsen) discloses the use of magnesium hydroxide slurry, made from a standard magnesium oxide, as the basis for a foliar spray as a carrier for active biocides for both insects and fungi where the benefits are associated with the ability of the alkaline particles to absorb active biocides to render them insoluble, and the strong adherence of the particles on the leaves of the plants such that the biocide can act over many washings of the leaf. That patent describes the role of the magnesium hydroxide as having no insecticidal or germicidal activity. In the context of this invention, the important teaching of that patent is the adherence of magnesium hydroxide.

This view was supported by a paper published by Motoike et al., "Antiviral activities of heated dolomite powder," *Biocontrol Sci.* 13(4):131-8 (2008), in which processed dolomite is shown to exhibit anti-viral activity. U.S. Patent Publication 2009/0041818 A1 claims an anti-viral agent that is a mixture of an oxide and a hydroxide, in which it is taught that hydroxide ions are produced by the reaction of the oxide with a hydroxide. It is claimed that many materials can provide the hydroxide, among which is $Mg(OH)_2$, and the oxide is preferably MgO. The relevant disclosure of this prior art is that the biocide activity of such conventional slurries is primarily transient and thus a manufactured magnesium hydroxide, or hydrated calcined dolomite slurry, does not have a significant long-term biocide effect. Without being limited by theory, this work suggests that the active chemical species in such a hydroxide slurry are naturally present, but their concentration is too low for a sustained impact on microbes. This disclosure seeks to overcome this limitation.

Insight into how the nano-$Mg(OH)_2$ has a significant bioactivity compared to standard materials is gained at two levels.

First, at the biological level, the most plausible theory of why pathological fungal growth is suppressed by chemical processes is the presence of Reactive Oxygen Species (ROS). ROS have a high redox-potential, and include the superoxide ion $O_2^{2-}$, which is known to generate hydroxyl radicals OH, perhydroxyl anions $HO_2-$ and hydrogen peroxide $H_2O_2$ by hydrolysis with water. There are equilibria between these species in water that is largely regulated by the pH, and at the pH near a nano-$Mg(OH)_2$ grain, around 10.4, the perhydroxyl anion dominates. Plants can ramp up the production of ROS as a defense against pathogenic microbial attack, with the ROS attacking the primitive cell walls of pathogenic fungus and bacteria. In response, fungus can produce chemical species that react and neutralize the ROS, and the ROS attacks and destroys the cell walls of pathogenic microbes. The same model for the activity is true of pathogenic bacteria, in particular, the anaerobic gram-negative bacteria. The ROS symbiosis is associated with the relationship between the plant ROS and the beneficial gram-positive bacteria, which are essential to a healthy environment for growth. Gram-positive bacteria are generally beneficial and aerobic, and the ROS increases the oxygen level in the environment. For example, as demonstrated in the case of rice blast fungus: Kun Huang, Kirk J. Czymmek, Jeffrey L. Caplan, James A. Sweigard and Nicole M. Donofrio (2011).

Second, at the atomic level, it is evident that the long-term biological activity of nano-$Mg(OH)_2$ slurry is associated with is ability to produce, and stabilize ROS. In general terms, small crystal grains have, by definition, a high proportion of their crystalline surfaces, which are formed at the high energy surfaces, and it is well understood that such surfaces are the source of energetic oxidants, such as the ROS species. In the case of $Mg(OH)_2$, techniques such as Electron Paramagnetic Resonance has detected all of the radical species described above on normal crystals, albeit at low concentrations. ROS radicals in solution can recombine, and the bio-activity impact of ROS would degrade by radial recombination. In the presence of $Mg(OH)_2$, the ROS rate of dissipation can be substantially reduced, if not suppressed, by the generation of magnesium peroxide $MgO_2$. Magnesium peroxide is a stable crystalline material, and is usually formed in a mixture with hydrogen peroxide $H_2O_2$, water and excess MgO. It is stable in this form at ambient temperature (I. I. Vol'nov and E. I. Latysheva, "Thermal stability of magnesium peroxide," Izvestiya Akademii Nauk SSSR, Seriya Khimicheskaya, No. 1, pp. 13-18, January, 1970). Therefore, nano-$Mg(OH)_2$ can not only form ROS at the grain boundaries but also the ROS species can be stabilized on the grain surfaces. The ROS species are stored on the nano-grain surfaces, and would be released by the change in the equilibria associated with a pathogen attack, and general dissolution of the nano-$Mg(OH)_2$ to supply magnesium to the plant as a fertilizer.

In summary, a reasonable model for the bioactivity of nano-$Mg(OH)_2$ is that each particle is a nanoscale crystalline grain that has a high concentration of ROS, which is stabilized on the energetic surfaces of the grain, and the bioactivity arises from the enhancement of the plant's own natural defense systems that form ROS to provide the aerobic environment that suppresses pathogenic microbes. This effect is enhanced by the pH of the $Mg(OH)_2$ at 10.4, which may neutralize acids extruded by pathogens; the net positive particle charge from hydrolysis, which attracts the particles to negatively charged surfaces of certain microbes and cells; and the adherence of the particles onto the surfaces of the microbes and cells of plants. By contrast, normal $Mg(OH)_2$ with grain sizes of 0.1 to 100 microns generally have surfaces that are dominated by the stable (001) surface, and the concentration of ROS would be small.

The same mechanisms ascribed above to nano-$Mg(OH)_2$ may apply to other bioactive materials based on metal oxides, such as nano-ZnO and AgO. Their nano-grains will also support a range of ROS species that depend on the specific defects at the respective grain boundaries. For example, nano-ZnO is known to produce peroxyl and hydroxyl radicals.

The mechanism for bio-activity of nano-grain particles is substantially different from most other fungicides and bactericides, which use toxic compounds to target pathogenic microbes. First, the mechanism of ROS lies at the core differentiation between aerobic and anaerobic microbes, and genetic evolution to limit the impact of the bio-activity is unlikely. Second, the mechanism is an enhancement of the natural processes whereby plants defend themselves against pathogenic attack. No new chemical species are involved, and the products of the decomposition are essential nutrients or micro-nutrients and, in the case of magnesium, it is an essential nutrient for the production of chlorophyll. Plants absorb magnesium through stomata on the leaves, and the aerobic/anaerobic contests between fungi, gram-positive and gram-negative microbes and the plant cells take place, both within the soil and on the leaves, for example, as described by Susan S. Hirano and Christen D. Upper, *Microbiol. Mol. Biol. Rev.* 64:3624-653 (2000).

A probiotic has been defined in a proceeding of the U.S. Patent and Trademark Office, Trademark Trial and Appeals Board, Serial No. 77758863 (2013), as a generic name for a fertilizer using friendly bacteria in the soil-producing microbial ecology means to bring back symbiotic relationships to the soil. In this application, the definition is extended to include symbiotic relationships on the plant leaves, and the symbiosis is specifically associated with the relationship between the plant and the beneficial gram-positive bacteria, which are essential to a healthy environment for growth. Indeed, when nano-$Mg(OH)_2$ is applied onto leaves as a folia spray, the impact of magnesium absorption as a fertilizer is noticeable through both the color from increased chlorophyll, and the increased leaf thickness. Thus, at a technical level, the properties of nano-$Mg(OH)_2$ satisfies the requirements of being a probiotic soil or plant amendment.

The means of production of nano-materials use chemical synthesis, and the materials are expensive to produce. Furthermore, the handling of very fine powders is difficult because these powders have a tendency to readily float in air. Most importantly, nano-materials are very difficult to filter from air using conventional air filters. Thus, the production processing of these materials requires expensive handling equipment to avoid loss of the materials and to meet safety, health and environmental regulations. These costs are such that nano-materials have not made a substantial impact in the markets for biocides. Equally important, there are concerns about nano-particles arising from their ability to be absorbed through the skin, and inhaled into the lungs, by virtue of their small size.

There is a need for a product that has the same desirable intrinsic biological activity of nano-materials using a process that can produce significant volumes of product, but also avoiding the handling issues of nano-materials, and their potential for absorption and inhalation.

Any discussion of the prior art throughout the specification should in no way be considered as an admission that such prior art is widely known or forms part of common general knowledge in the field.

BRIEF SUMMARY

Problems to be Solved

A problem to be solved may include the production of materials that have a high concentration of bio-active species as do nano-particles, but which do not have the undesirable features of nano-particles arising from their small size. It is an object of this disclosure to overcome this disadvantage of the prior art.

A possible means for solving the problem is to, as a first step, produce a porous nano-grain composite powder in which the particles in the powder are composed of crystalline nano-grains of material, where the grain size of an nano-grain is on the nano-scale so as to generate the active species responsible for biological activity.

The powder may be used directly, or may be hydrated in water to form a slurry concentrate that can be diluted in water and sprayed to provide protection against microbial activity.

The material on which the powder or spray is applied may be an agricultural or an aquaculture crop, or a product such as seeds, vegetables, meat, or fish, or a processed food product; or may be a surface that is to be decontaminated. It may be applied as a soil or plant amendment.

The particles are required to be sufficiently porous, so that, in contact with the microbes, the ROS species are made readily available to the particle surface by diffusion, and/or by dissolution of the particle when applied to the product as a means of controlled release to produce a sustained biological impact.

The particle size is preferably such that the powders are not breathable, and cannot diffuse through the skin. Such particles are on the scale of 10-100 microns, and are easily handled and processed by users.

The binding of the particles is such that they are mechanically stable, and do not readily degrade to nano-particles that can be breathed or absorbed through the skin. The particles are not weakly bonded aggregates of single nano-grain particles.

The particles are to be sufficiently porous that the ROS species formed and stabilized on the grain surfaces can diffuse to, and impact on, microbes such as virus, bacteria and fungus in the powder or hydrated form. The nano-composite is purposefully not an aggregation of nano-particles, but is a material in which the constituent gains are strongly bonded to each other, so as to resist mechanical disaggregation. A porosity of about 0.5 for the particles in the powder may be desirable.

It is advantageous that the material is an oxide, such that the defect species formed have a high oxidizing power as measured by their redox potential; and it is further desirable that the material has a basic pH such that it is gradually degraded in the acidic media in which microbes thrive, so that fresh surfaces are continuously exposed so that the bioactive response is maintained for a length of time until the particles are dissolved.

It may be advantageous that the material from which the nano-composite is produced by the process described herein is a mineral.

It may be advantageous that the surfaces of the nano-composite material, as a powder or a hydrated material, adhere to both microbes and to cell walls to initiate the desired activity to protect the material, and to minimize the loss of material from the application of water.

It may also be advantageous that the hydrated nano-composite material is not toxic to humans when and if consumed in small amounts, so that the material may not be required to be washed off the product before consumption. When applied to plants, it is even more preferable that the nano-composite degrades to a fertilizer and is absorbed by the plant as a nutrient.

Means for Solving the Problem

A first aspect of this disclosure includes a process that utilizes the following steps to make the bioactive material:

a) Preparing a precursor material that is an inorganic compound powder that contains one or more volatile constituents such as $CO_2$, in the form of metal carbonates, $H_2O$ in the form of metal hydroxides, bicarbonates, and $NH_3$, in the form of amines or organic ligands such as acetates or oxylates, such that, when heated these constituents are driven off to give an oxide powder that has a high porosity, preferably in the range of 0.5 or higher. The powder formed by heating is a metal oxide, which generally will have a known biological activity as a conventional nano-material, such as magnesium oxide or zinc oxide. The standard measure of volatility of the precursor is the loss on ignition when heated to a temperature of less than 1000° C. The loss on ignition should preferably be about 50% of the precursor mass. There is a wide variety of production techniques to make such inorganic precursor compounds, in which the powder is prepared as a crystalline material, often precipitated from an aqueous solution, and which is ground to the desired particle size of 10-100 microns. An alternative approach is to grind mineral precursors, such as metal carbonates, hydroxides or hydroxycarbonates. As an example, magnesium oxide mineral precursors include magnesite ($MgCO_3$), Brucite ($Mg(OH)_2$), Hydromagnesite($4MgCO_3.Mg(OH)_2.4H_2O$), and Nesquehonite ($MgHCO_3.OH.H_2O$), among others. Compounds include Magnesium Citrate $Mg(C_6H_6O_7)$, and Magnesium Oxalate $Mg(C_2O_4)$. All these compounds decompose on heating to form MgO. Mixed metal compounds can be either produced, or found as minerals, often as double salts, such a dolomite.

b) Calcining the precursor to produce a porous nano-composite oxide powder. The requirement of the flash calcining process is to rapidly vaporize the volatile constituents to yield particles with the properties:
   (i) A particle size distribution in the range of 10-100 microns, as measured, for example, by light scattering using shear mixing to ensure that the particles are not weakly bonded aggregates of conventional nano-particles;
   (ii) A high porosity (from the voids left by the volatile constituents);
   (iii) A nano-crystalline structure in which the characteristic length of the grains is on the nanoscale, preferably 20 nm or less, as measured by the broadening of the X-ray diffraction bands;
   (iv) A surface area in the vicinity of 150 $m^2$/gm or higher, as measured, for example, by the Brunauer-Emmett-Teller (BET) method.

The surface area and porosity may be determined by techniques such as the Barrett-Joyner-Halenda (BJH) method, and by Small Angle X-Ray Scattering (SAXS). An important condition of the calcination process to produce these properties is that it occurs at a low temperature with a sufficiently small residence time that the particles do not sinter during production, as such sintering rapidly leads to a loss of the desirable properties. The particles may decrepitate during this production process, and such decrepitation is tolerable and can be controlled by the design of the calcination process and the selection of the precursor.

An example of a continuous production process includes the calciner disclosed by Sceats and Horley in Published PCT Patent Application No. WO2007/045048 and included herein in its entirety, in which the process occurs in a counterflow indirect heating process, and the reaction is complete in several seconds by the use of sufficiently high temperature. Another example is a batch production process in which the calcination takes place at a low temperature under vacuum over a long period of time.

c) Hydrating the powder to produce a stable hydroxide slurry with a high solids fraction, preferably in the range of 50-60%. The desirable property of the slurry is that it does not settle rapidly, exhibits minimal syneresis, and has a low viscosity for dosing into a spraying system for many applications. The hydration process is one in which the hydrated product is also a nano-composite material. Such properties can be measured by drying the slurry, and measuring the same properties as considered previously for the calcined powder. The objective of the hydration process can be met by ensuring that the hydration occurs within the particle such that the nano-crystals form the hydroxide directly, rather than the traditional process where the hydroxide is precipitated from the solution as crystals. The slurry composition to achieve this process may require the use of co-solvents, temperature and pressure, to prevent the precipitation mechanism. The objective is to ensure that the hydrated material contains the high energy surface defects that are responsible for the bio-activity. Such defects occur on the hydrated grain boundaries, and the confined hydration ensures that the concentration of the surface defects is maximized. An example of the hydration process is that disclosed by Sceats and Vincent, for example, in AU 2013/904096 (incorporated herein by reference).

This disclosure may also provide for a magnesium oxide powder or slurry material that has long-lived biocide activity, and the process and apparatus for production of such biocide slurries. In one form, the disclosure provides an intrinsic biocide slurry or powder comprising particles in the range of 0.5-100 microns that have been processed to be a bonded aggregate of nano-crystalline hydroxide or oxide crystallites. When slurried in water, additives are used to stabilize the slurry to give a long lifetime and a low resistance to shear thinning. The crystallites are characterized by a high fraction of defects derived from superoxides formed in the production process. The mineral precursor is preferably the mineral magnesite or dolomite.

In another form or aspect of this disclosure, the biocide response is enhanced by adding adjuvant toxins including hydrogen peroxide, or ozone or traditional molecular biocides or nano-particles that preferably absorb in the particles and enhance the intrinsic biocidal properties.

In another form, the powder may be spread to provide an insecticide through its dehydration effect, and the powder continues to provide a biocidal response after hydration. The biocide benefits are specific to the intended application, where the response to either or both dehydration and superoxide-derived defects may play a role as an insecticide, fungicide, bactericide or viracide. For example, in the storage and shipping of grains, it is preferable to maintain a low water vapor atmosphere, so that a non-toxic biocide powder that achieves biocide action through dehydration would be desirable. In other applications, such as an additive to processed food that has high water content, the application of a slurry product would generally be desirable.

In another form, the powder may be used in industrial applications for which a nano-grain composite material may have advantageous properties, such as, for example, catalyst substrates and the like.

The powder or slurry product has preferably a shelf lifetime of several months, and can be used as a feedstock for production of (a) a foliar spray for agricultural application, or (b) an additive to food as an intrinsic non-toxic biocide, or (c) as an additive to a fiber or polymer substrate to make a gauze or a wipe, or (d) dried to produce a powder or a granular form, or (e) mixed with oils to form an emulsion, or (f) aerated to produce a foam or fog, or (g) catalyst substrates.

A further aspect of this disclosure includes a process for producing a biocide powder or a chemical detoxifier powder from a carbonate compound, including the steps of: grinding the mineral to produce a powder with a broad particle size distribution in the range of about 1-100 microns, with a mean particle size of optionally about 10-20 microns, preferably about 10 microns; calcining the powder in an externally heated counterflow flash calciner to produce an oxide with a high surface area and a high degree of calcination.

This preferred process for producing a biocide slurry or a chemical detoxifier slurry from a powder may also include forming a stable, readily thinned, slurry of the hydrated oxide with about 60% solids in the final product after hydration, by the process of mixing the powder with water, under conditions in which the temperature is maintained at or near the boiling point of water until the hydration is completed, shear mixing is applied, and a carboxylic acid or salt is added as the thinning agent; quenching the slurry to below 60° C.; cooling the slurry to ambient temperature; and adding additives to enhance the biocidal properties.

The preferred carbonate compound is magnesite, in which case, the surface area of the oxide is preferably greater than 150 $m^2$/gm, and even more preferably greater than 190 $m^2$/gm, with the degree of calcination being preferably greater than 90%. Preferably, the carbonate compound may also be dolomite, in which case, the degree of calcination is set to produce Semidolime $MgO.CaCO_3$, with a surface area preferably greater than 30 $m^2$/gm.

Preferably, the carbonate compound may also be a Magnesium Hydrocarbonate, including Hydromagnesite or Nesquehonite, in which case, the degree of calcination is set to produce magnesium oxide MgO, with a surface area preferably greater than 230 $m^2$/gm. Preferably, the carboxylic acid may also be acetic acid, and the carboxylic salt is magnesium or calcium acetate. The preferred additive may be an aqueous solution of hydrogen peroxide. The preferred additive may also be ozone, which is sparged into the slurry. Further, the preferred additive may be a molecular or nano-particle biocide. Preferably, the additive is a dispersant.

Preferably, the slurry or powder is used to produce any of a spray, or mixed with oil to form an emulsion, or processed into a foam or fog.

A further aspect of this disclosure includes a reaction apparatus for producing a biocide powder or a chemical detoxifier powder from a carbonate mineral, including: a grinder for carbonate minerals; an externally heated counterflow flash calciner that produces high surface area oxides from the ground carbonate.

Preferably, the reaction apparatus for producing a biocide slurry or a chemical detoxifier slurry from a powder produced by the reaction apparatus includes: a reaction vessel having an inlet for caustic calcined carbonate powder and a water inlet; a shearing apparatus for shearing the reaction mixture; and a steam outlet for release of steam from the reaction vessel, such that in use, the reaction is controlled by allowing heat of hydration to raise the temperature of the reaction mixture, allowing water to boil off from the reaction mixture as hydration proceeds, and removing steam via the steam outlet to remove excess heat and control the reaction temperature at the boiling point, a means of quenching the slurry to below 60° C., preferably by transfer of the slurry to a cooled container; a means of cooling the slurry to ambient temperature; a means of adding solid or liquid additives to the slurry if required; and a means of sparging the slurry with ozone if required.

A further preferred aspect of this disclosure includes a chemical composition adapted for use as a biocide, wherein the composition comprises: a sprayable slurry of particles of calcined powder suspended in water, wherein the particles have a porosity of greater than 0.5 and wherein the surface of the particles includes microstructures defined by at least one nano-crystalline structure positioned on the outer surface of the particles. Preferably, the calcined powder is magnesite.

The preferred particles may be adapted to allow the microstructures to be released from the surface of each particle over a predefined time interval. Further, the preferred particles may form nano-particles adapted to provide a high redox potential.

Further forms of the disclosure will be apparent from the description and drawings, and from the claims.

In the context of this disclosure, the words "comprise," "comprising" and the like are to be construed in their inclusive, as opposed to their exclusive, sense, that is, in the sense of "including, but not limited to."

The disclosure is to be interpreted with reference to the at least one of the technical problems described or affiliated with the background art. The present disclosure solves or ameliorates at least one of the technical problems and this may result in one or more advantageous effects as defined by this specification and described in detail with reference to the preferred embodiments of the present disclosure.

BRIEF DESCRIPTION OF THE DRAWING

Embodiments of the disclosure will be better understood and readily apparent to one of ordinary skill in the art from the following written description, by way of example only, and in conjunction with the drawing, in which.

DETAILED DESCRIPTION

Preferred embodiments of the disclosure will now be described with reference to the accompanying drawing and non-limiting examples.

Figure 1:
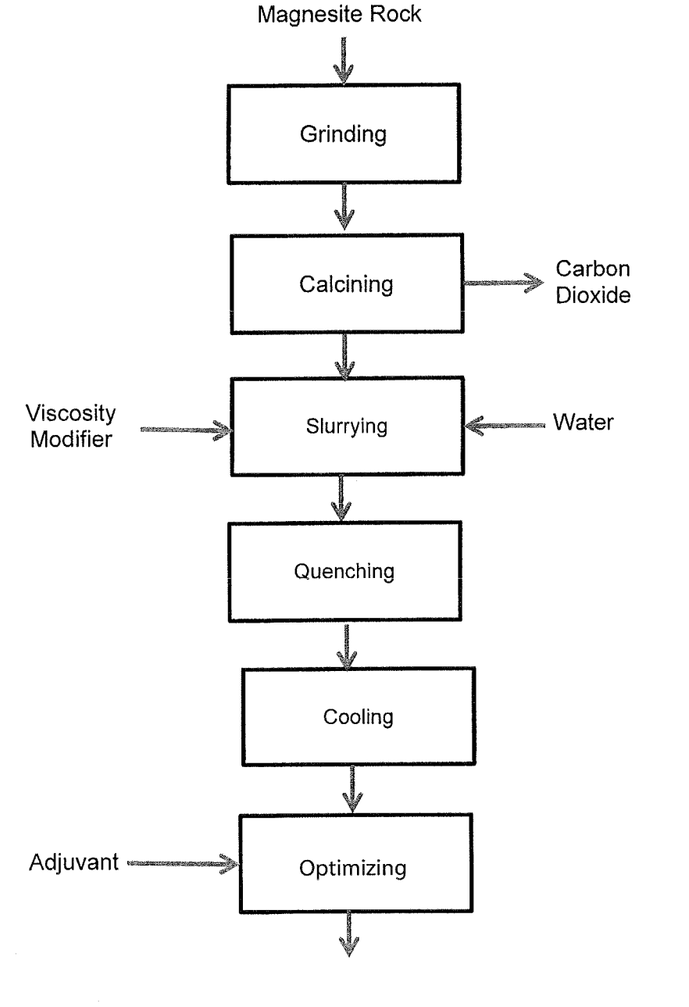
FIG. 1 shows a schematic drawing of a process for production of stable, thin, high solids biocide slurry from powders of caustic calcined magnesia.

One example form of manufacture of the product can be described by consideration of the process flow of FIG. 1 for the case of magnesium hydroxide as a probiotic or biocide.

In this embodiment, the first step is one in which the carbonate mineral is magnesite, substantially $MgCO_3$, which is crushed and ground to the particle size distribution that is close to that of particles found in the end product. This may be set by the cut-off of the classifier, and the residence time in the grinder. Typically, the ground material will have a lower particle size of about 1 micron, and upper particle size of about 100 microns, and an average particle size in the range of 10-20 microns. If required, impurities in the mineral such as sand, talc and magnetic particles are extracted during this process. The exact distribution depends on the mineral source, whether macrocrystalline or cryptocrystalline, the impurities, the grinder and the grinder settings. Most importantly, it is noted that there is no specification that there are any nano-crystalline particles present (i.e., with a diameter less than 0.1 micron) and, generally, such particles are undesirable because, as fines, they are difficult to filter from the grinder air, and also to process in the steps described below, and to meet customer and community concerns about the toxicity of nanoparticles in general. The grinder is preferably a mill that entrains the ground particles in air and that removes particles above 1 micron before they can be further ground. This is a known art per se.

The second step of the process is that of calcination in which the magnesite is calcined. It is important that the processed particles exhibit minimal sintering during the calcination process, and achieve a degree of calcination that is preferably in excess of 95%. The most fundamental measure of the impact of sintering is the specific surface area. This should be greater than 150 $m^2/gm$ and preferably greater than 190 $m^2/gm$. The powder XRD analysis of the MgO exhibits a line broadening, which is a measure of the crystalline structure of the particle, and for a powder with the surface areas quoted, that width corresponds to a crystalline order of about 20 nm or less. This is the same XRD profile observed in nano-materials. However, by contrast, the particle size of the nano-MgO is commensurate with the crystallinity of the powder, whereas, with the product of this disclosure, the particle size is several orders of magnitude higher than the crystallinity, i.e., about 10 microns compared to 20 nm. The basic assertion of this disclosure is that the biocide or probiotic activity arises from the crystallinity, rather than the particle size.

The type of calciner is critical to achieving the properties described above. The basic requirement is that the process is very fast to eliminate the effect of sintering, and this should preferably be several seconds. This means that the process is flash calcination. The second requirement is that the particles experience the lowest possible temperature during this time. Conventional flash calciners drop the particles into a very hot combustion gas, and from that time, the temperature of the gas decreases as the reaction extracts energy from the gas stream. Further, not all particles experience the same conditions. The net result is that the outer surfaces of the particles are extensively sintered, and it is difficult to achieve surface areas in excess of 50 $m^2/gm$. The small particles are most extensively sintered. The preferred calciner is that described by Sceats and Horley, for example, in WO2007/112496 (incorporated herein by reference), to give a powder with a surface area preferably 150 $m^2/gm$ or larger, in which indirect counterflow heat is used. In this case, the temperature of the particles flowing through the calciner steadily increases for all particles, and the maximum temperature they experience is the exhaust temperature. During the calcination, there is generally some decrepitation of the input particles, and often a shoulder appears on the particle size distribution in the region of 0.1-1 micron. Control of the external burners along the calciner provides the desired heat transfer to the particles, and the degree of calcination and surface area can be controlled. This system is known per se, and is capable of operating at production levels of about 5 tonnes per hour (50,000 kg/h) for particles that are 95% calcined with a surface area of 190 $m^2/gm$, and a crystallinity of 20 nm, and negligible particles below 0.1 micron. These particles are strong, resist grinding and do not significantly disaggregate by ultrasonification. The particles are not agglomerates of nano-particles. The crystallites, albeit porous, are strongly bonded.

The important factor that determines the biocidal impact is the high surface area of the calcined powder. There is a range of stable magnesium hydrocarbonate compounds such as hydromagnesite and nesquehonite of the form $(MgCO_3)_x(Mg(OH)_2)_y(H_2O)_z$ that contain very large volume fractions of $H_2O$ and $CO_2$, and when these materials are calcined, they produce very high surface area magnesium oxide, on the order of 500 $m^2/gm$. These compounds can be found as rare minerals, or can be synthesized by sparging $CO_2$ into magnesium hydroxide slurry described below, separating and drying the powder prior to calcination. This approach provides a material with a high biocidal impact.

The powder product from these two process steps may be used as a biocide powder, where the desirable properties of dehydration are required. Where a slurry product is desirable, the third step of the process is to hydrate the slurry.

This process is well described by Sceats and Vincent, for example, in AU 2013/904096 (incorporated herein by reference), as a process that can produce tonnes of slurry per hour to match the production rate of the calciner described above. The high surface area of the particles is such that the hydration reaction, when mixed vigorously, liberates a large amount of heat and boils the water. This establishes a set point and the thermally activated hydration occurs at the boiling point, and the excess heat is liberated by boiling. The application of a shear mixer provides the agitation required for a uniform controlled process. During the course of the reaction, acetic acid is added to the slurry to provide thinning necessary for the shear mixer to operate. The reaction is complete when the temperature starts to drop from the heat losses. It is preferred to quench the slurry quickly below 60° C., and then let the slurry cool to ambient temperature for the next processing step. The net result is a slurry that has hydrated and is stable over many months with regard to sedimentation, and which is readily shear thinned to allow pouring and processing. This slurry has the same intrinsic biocide activity as has nano-particles when diluted in water for application as a foliar spray. This will be considered below. Importantly, there is no significant loss of biocide activity during over the slurry lifetime of several months.

The fourth step, if required, is to add adjuvants to either the powder or slurry product in order to increase the biocide properties above that of the intrinsic biocide response considered below. There are many such adjuvants. These can be hydrogen peroxide, or ozone, which can be added to saturate the crystalline binding sites on the $Mg(OH)_2$ surfaces with the radical species being the superoxide ion, the hydroperoxide anion, and oxygen radical, and the hydroxyl radical. In addition, the acetate ions may be further converted to the peroxyacetate ion, which is stable at the pH of the slurry, at about 10.4. Impurity ions, such as $Fe^{2+}$ and $Fe^{3+}$ will have been removed during grinding to reduce oxygen degradation of these radicals. The use of hydrogen peroxide or ozone supplements the intrinsic radicals developed during calcination and hydration. Ozone is added by sparging the slurry with ozonated air. Other adjuvants include a large number of established biocides, including all those listed in U.S. Pat. No. 6,827,766 B2 or nano-particles such as AgO and ZnO. Depending on the specific adjuvant and the amount added, the stability of the slurry may have to be re-established by the addition of dispersion agents. The use of adjuvants is not generally preferred because it may make the product toxic to humans, and increase the cost of production compared to the intrinsic biocide developed in the previous steps.

The intrinsic biocide produced using steps 1-4 described above produces either a powder of magnesium oxide or a 60% solids slurry of magnesium hydroxide particles with a range of particle sizes from 0.4 micron to 50 microns as measured by a particle size analyzer. For the slurry, the particles are confirmed to be magnesium hydroxide by drying the slurry at about 100° C., and measuring the TGA and DSC, and comparing these with analytical grade magnesium hydroxide. The nano-crystallinity of the particles of magnesium oxide or magnesium hydroxide is measured from the line broadening of diffraction peaks from the dried slurry using Scherer's formula to be 20 nm. The appearance of the dried magnesium hydroxide powder product under an SEM reveals particle shapes not unlike those of the porous MgO powder produced by calcination, with the pores filled in by the reaction with water. The surface area of the MgO powder was measured to have a BET surface area of 190 $m^2/gm$, while that of the dried magnesium hydroxide slurry was 20 $m^2/gm$.

The biocide activity of the intrinsic slurry has been established using in vitro measurements and in preliminary crop trials. For in vitro studies, the slurry is diluted to 1% by the addition of water, and is sprayed into a prepared Petri dish in which a dot of the fungus, bacteria, or virus strain under test has been incubated and grown over 24 hours. The rate of growth of the radius is measured over a period, and the biocidal impact is measured by the extent that the ring growth rate has been suppressed. Studies were completed on a number of fungi, and a broad-spectrum antifungal impact was observed, and is comparable to commercial fungicides.

For preliminary crop trials, a number of crops such as grapes, avocados and bananas exhibiting fungal outbreaks were sprayed with the diluted slurry, and the biocidal impact measured by the healthiness of the crop, especially with regard to the presence of fungi, was compared to a field that was not sprayed. On inspection, after 7 days, the fungi were not observable on the sprayed area. It was noted that the powder had a strong adherence to leaves, and that the leaf appearance had improved indicating that the magnesium was being adsorbed into the plant and promoting greater photosynthesis. Such leaf characteristics include the color and leaf thickness.

In trials of insecticide response, a sample of insect-ridden wheat was dusted with magnesium oxide powder. After several days, the insect count had decreased considerably, and with a response that was similar to dehydrated diatomaceous earth.

It is apparent that the diluted slurry has similar biological activity as reported for nano-magnesium hydroxide. Without being bound by theory, it follows that the similarity of the nano-crystalline grain properties of the MgO powders of this process, and the crystalline properties of the single grain nano-MgO are the common feature. The established propensity of crystal surfaces of MgO and $Mg(OH)_2$ to stabilize radical species such as superoxide, hydroxyl, atomic oxygen, and peroxyhydroxide that are known to be active in breaking down the primitive epithelial cell walls of microbes is the most likely explanation for this property. The high density of these sites and the stabilization properties provide the basis for the long-lived performance of the slurry, and explain their resistance to decomposition of these radicals to produce oxygen, which would otherwise have diminished the effectiveness over time. It is also apparent that the trials with the powder product provided an insecticide response that was typical of dehydration. Without being bound by theory, the response may be a combination of dehydration and the superoxide response.

Naturally, the ability of the large particles to make intimate contact with the surfaces of microbes is less than that of nano-particles. However, all particles of MgO have negatively charged surfaces, and the activity against gram-negative and gram-positive microbes suggests that intimate contact is not required. A more likely explanation is that the radical species are in equilibrium with the water, and transfer by diffusion from the particle to the microbe. In the case of slurries, it is the surface area of the hydroxide particles that will control the process, and it is noted that the surface area of hydrated nano-particles is of the order of 30 $m^2/gm$, a similar result as measured for the powders reported herein. The reports of increased activity of smaller nano-particles may simply be a reflection of the increased geometric surface area of smaller particles. It is noted that the propensity of nano-particles to aggregate is well established, and diagnostic tests of the particle size is performed by ultrasonification of the dispersion before measurement of particle size. The nano-powders in suspension deliver their biocide activity as aggregates. This is not inconsistent with the premise of this disclosure that the particle size is not the origin of the biocide properties. In the case of dehydration, the magnesium oxide particle surface is about 190 m$^2$/gm. The high rates of dehydration are linked to the surface area and, in addition, the particle surface is very rough, and able to penetrate the exoskeleton of insects.

The targets are not only microbes described above, but also chemicals. A different application of the slurry is to deactivate toxic chemicals that would otherwise harm plants, animals and humans. Nano-MgO has been used for this purpose, as a source of radical species that attack and passify many such agents, such as those that can be deployed as chemical and biochemical warfare agents. This is because many such chemicals achieve their toxic effect by free-radical generation, and the slurry, or a dispersed slurry is a carrier of free radicals that can react and destroy these compounds. The magnesium oxide power or slurry may be used to deactivate such chemicals.

The slurry described in this disclosure is not generally deployed as a biocide at 60% solids. It is a concentrate that is used to make biocides for different applications. The means of application of biocides in agriculture is preferably through a sprinkling system to avoid losses to the crop from wind. A common means is to use a slurry of the materials, which is diluted by the spray water to about 1%. This foliar spray approach has wide industry acceptance. In that case, a material based on magnesium hydroxide has an added benefit of providing a source of magnesium, which is an essential nutrient for photosynthesis. A spray should preferably have particles that are less than 100 microns, and preferably 25 microns, diameter to avoid blockage of the nozzle. The use of a spray may also be applicable for medical applications. However, in that area, there is also an application for the incorporation of the material in a mask to reduce infection from airborne microbes, or a wipe to remove microbes from surfaces.

MgO-laced gauze or other fabric materials can be made by reacting the powder or a slurry of the material with various polymer-forming materials and applying the mixture to set on fabrics, with the objective being to adhere the particles on the gauze. In another area of application, in the food industry, the non-toxic biocide magnesium hydroxide slurry may be added into liquid products, or may be added as a powder to dried products. There are known arts for slurry processing, such as grinding the dried product using conventional processes to generate the desired particle size, or producing granules by binding with appropriate materials suited for the application. It is noted that the MgO powder may be applied to food because the process of hydration can occur by virtue of the food product itself. In another application, the product should be able to be dispersed into a spray, or fog, or foam to give a large area coverage, for example, with spillages of toxic chemicals.

In another application, the slurry should be mixed with existing biocides as adjuvants. This includes conventional water-soluble biocides, typically molecular, that adsorb onto the particle to deliver a desired biocide activity. The formation of emulsions with oils that contain oil-soluble adjuvants is another such application.

Magnesium oxide is one particular oxide material that can be used, that has the benefit of availability of a mineral precursor. Another embodiment uses dolomite in which the degree of calcination of the magnesium site and the calcium site is controlled to give the desired biocidal properties.

In this specification, the word "comprising" is to be understood in its "open" sense, that is, in the sense of "including," and, thus, not limited to its "closed" sense, that is the sense of "consisting only of." A corresponding meaning is to be attributed to the corresponding words "comprise," "comprised" and "comprises" where they appear.

While particular embodiments of this disclosure have been described, it will be evident to those skilled in the art that the present disclosure may be embodied in other specific forms without departing from the essential characteristics thereof. The present embodiments and examples are, therefore, to be considered in all respects as illustrative and not restrictive, with all changes that come within the meaning and range of equivalency therefore intended to be embraced therein. It will be further understood that any reference herein to known prior art does not, unless the contrary indication appears, constitute an admission that such prior art is commonly known by those skilled in the art to which the disclosure relates.

In this specification, references to the term "probiotic" mean any material adapted to beneficially promote or enhance the microbial balance within the treated area, location or place.

A probiotic is also a generic name for a fertilizer using friendly bacteria in the soil producing microbial ecology means to bring back symbiotic relationships to the soil. In this application, the definition is extended to include symbiotic relationships on the plant leaves, noting that plants absorb applied magnesium as a fertilizer through the leaf stomata. Indeed, when sprayed onto leaves as a folia spray, the impact of magnesium absorption as a fertilizer impact is noticeable through both the color from increased chlorophyll, and the increased leaf thickness. The most plausible theory of why pathological fungal growth is suppressed is the presence of Reactive Oxygen Species. Plants can ramp up the production of ROS as a defense against microbial attack, with the ROS attacking the primitive cell walls of fungi. In response, the fungi can produce chemical species that react and neutralize the ROS. See, for example, in the case of rice blast fungus: Kun Huang, Kirk J. Czymmek, Jeffrey L. Caplan, James A. Sweigard and Nicole M. Donofrio (2011) "Suppression of plant-generated reactive oxygen species is required for successful infection by the rice blast fungus," *Virulence* 2:6559-562, DOI: 10.416 l/viru.2.6.18007. The ROS attacks and destroys the cell walls of pathological fungi. The same model for the activity is true of pathogenic bacteria, in particular, the anaerobic gram-negative bacteria. The symbiosis is associated with the relationship between the plant and the beneficial gram-positive bacteria, which are essential to a healthy environment for growth. These bacteria are aerobic, and the ROS increases the oxygen level in the environment. Such bacteria exist in the soil and on the leaves. See, for example, "Bacteria in the Leaf Ecosystem with Emphasis on *Pseudomonas syringae*—a Pathogen, Ice Nucleus, and Epiphyte," Susan S. Hirano and Christen D. Upper, *Microbiol. Mol. Biol. Rev.* September 64, 3624-653 (2000). The probiotic effect is that the addition of nano-grains or nano-grain composites of Mg(OH)$_2$ increases the supply of ROS above that which the plant provides. The slow dissolution of the grains by the acid environment leads to a sustained supply of ROS for a long-lasting biological activity. No new chemicals are introduced in the process.

Although the disclosure has been described with reference to specific examples, it will be appreciated by those skilled in the art that the disclosure may be embodied in many other forms, in keeping with the broad principles and the spirit of the disclosure described herein.

The present disclosure and the described preferred embodiments specifically include at least one feature that is industrial applicable.

The claims defining the invention are as follows:

1. A process for producing a biocide powder or a chemical detoxifier powder or a catalyst support from a carbonate compound, comprising the steps of:
    a) grinding the mineral to produce a powder with a broad particle size distribution in the range of 1-100 microns, with a mean particle size of 10-20 microns;
    b) calcining the powder in an externally heated counterflow flash calciner to produce an oxide with a high surface area, high porosity, and a high degree of calcination;
    c) forming a stable, readily thinned, slurry of the hydrated oxide with about 60% solids in the final product after hydration, by the process of mixing the powder with water, under conditions in which the temperature is maintained at or near the boiling point of water until the hydration is completed, shear mixing is applied, and a carboxylic acid or salt is added as the thinning agent;
    d) quenching the slurry to below 60° C.;
    e) cooling the slurry to ambient temperature; and
    f) adding additives to enhance the biocidal properties.

2. The process of claim 1, wherein the carbonate compound is magnesite, with a surface area of the oxide being greater than 150 $m^2$/gm, with the degree of calcination being preferably greater than 90%.

3. The process of claim 1, wherein the carbonate compound is dolomite, wherein the degree of calcination is set to produce semidolime $MgO.CaCO_3$, with a surface area greater than 30 $m^2$/gm.

4. The process of claim 1, wherein the carbonate compound is a magnesium hydrocarbonate, and the degree of calcination is set to produce magnesium oxide MgO, with a surface area greater than 230 $m^2$/gm.

5. The process of claim 1, wherein the carboxylic acid is acetic acid, and the carboxylic salt is magnesium or calcium acetate.

6. The process of claim 1, wherein the additive is an aqueous solution of hydrogen peroxide.

7. The process of claim 1, wherein the additive is ozone, which is sparged into the slurry.

8. The process of claim 1, wherein the additive is a dispersant.

9. The process of claim 1, wherein the slurry or powder is used to produce a spray, or mixed with oil to form an emulsion, or processed into a foam or fog.

10. A reaction apparatus for producing a biocide powder or a chemical detoxifier powder or a catalyst support from a carbonate mineral, comprising:
    a. a grinder for carbonate minerals;
    b. an externally heated counterflow flash calciner that produces high surface area oxides from the ground carbonate;
    c. a second reaction vessel having an inlet for caustic calcined carbonate powder and a water inlet;
    d. a shearing apparatus for shearing the reaction mixture;
    e. a steam outlet for release of steam from the reaction vessel, such that, in use, the reaction is controlled by allowing heat of hydration to raise the temperature of the reaction mixture, allowing water to boil off from the reaction mixture as hydration proceeds, and removing steam via the steam outlet to remove excess heat and control the reaction temperature at a boiling point;
    f. a means of quenching the slurry to below 60° C.;
    g. a means of cooling the slurry to ambient temperature;
    h. a means of adding solid or liquid additives to the slurry; and
    i. a means of sparging the slurry with ozone.

11. A chemical composition adapted for use as a biocide, comprising:
    a sprayable slurry of particles of calcined carbonate powder suspended in water, wherein the particles have a porosity of greater than 0.5 and wherein the surface of the particles includes microstructures defined by at least one nano-crystalline structure positioned on the outer surface of the particles.

12. The chemical composition of claim 11, wherein the carbonate powder is magnesite.

13. The chemical composition of claim 12, wherein the particles are adapted to allow the microstructures to be released from the surface of each particle over a predefined time interval.

14. The chemical composition of claim 13, wherein the particles form nano-particles adapted to provide a high redox potential.

15. The process of claim 2, wherein the surface area of the oxide is greater than 190 $m^2$/gm.

16. The process of claim 2, wherein the additive is a dispersant.

17. The process of claim 3, wherein the additive is a dispersant.

18. The process of claim 2, wherein the slurry or powder is used to produce a spray, or mixed with oil to form an emulsion, or processed into a foam or fog.

19. The process of claim 3, wherein the slurry or powder is used to produce a spray, or mixed with oil to form an emulsion, or processed into a foam or fog.

20. The process of claim 4, wherein the slurry or powder is used to produce a spray, or mixed with oil to form an emulsion, or processed into a foam or fog.

* * * * *